US012734140B1

(12) United States Patent
Ciullo

(10) Patent No.: US 12,734,140 B1
(45) Date of Patent: Sep. 15, 2026

(54) METHODS FOR TREATING BONE AND NEUROPATHIC PAIN WITH CAPSAICIN

(71) Applicant: James Ciullo, Chicago, IL (US)

(72) Inventor: James Ciullo, Chicago, IL (US)

(*) Notice: Subject to any disclaimer, the term of this patent is extended or adjusted under 35 U.S.C. 154(b) by 4 days.

(21) Appl. No.: 19/396,629

(22) Filed: Nov. 21, 2025

(51) Int. Cl.
*A61K 31/165* (2006.01)
*A61P 25/02* (2006.01)

(52) U.S. Cl.
CPC ............ *A61K 31/165* (2013.01); *A61P 25/02* (2018.01)

(58) Field of Classification Search
CPC .............................. A61K 31/165; A61P 25/02
See application file for complete search history.

(56) References Cited

U.S. PATENT DOCUMENTS

2014/0134261 A1* 5/2014 Singh .................. A61K 9/4866 514/552

OTHER PUBLICATIONS

Borsook et al., "Surgically-Induced Neuropathic Pain (SNPP)", 2013, Ann Surg., 257(3): 403-412 (Year: 2013).*

Mankowski et al., Effectiveness of the capsaicin 8% patch in the management of peripheral neuropathic pain in European clinical practice: the ASCEND study, BMC Neurology, 2017, pp. 1-11, 17:80.

Olusanya et al., Capsaicin 8% Patch for Spinal Cord Injury Focal Neuropathic Pain, a Randomized Controlled Trial, Pain Medicine, Jul. 7, 2022, pp. 71-78, 24(1).

Giaccari et al., Capsaicin 8% Patch and Chronic Postsurgical Neuropathic Pain, Journal of Personalized Medicine, Sep. 27, 2021, pp. 1-9, 11,960.

Freynhagen et al., Narrative review of the efficacy and safety of the high-concentration (179 mg) capsaicin patch in peripheral neuropathic pain with recommendations for clinical practice and future research, Pain Reports, 2025, pp. 1-15, 10 e1235.

Finnerup et al., Pharmacotherapy for neuropathic pain in adults: a systermic review and meta-analysis, Lancet Neurol, Jan. 7, 2015, pp. 162-173, vol. 14.

Fields et al., Postherpetic Neuralgia: Irritable Nociceptors and Deafferentation, Neurobiology of Disease, Sep. 1, 1998, pp. 209-227, 5.

Fields et al., Post-Herpetic Neuralgia: Pathophysiology and Treatment, JJSPC, 1999, pp. 1-9, vol. 6 No. 1.

Uceyler et al., High-Dose Capsaicin for the Treatment of Neuropathic Pain: What We Know and What We Need to Know, Pain Therapy, Jul. 29, 2014, pp. 73-84, 3.

Altman, Topical Therapy for Osteoarthritis: Clinical and Pharmacologic Perspectives, Clinical and Pharmacologic Perspectives, Postgraduate Medicine, Mar. 2015, p. 139-147, 121:2, Taylor & Francis Group.

Schug, APM:SE Working Group of the Australian and New Zealand College of Anaesthetists and Faculty of Pain Medicine (2020), Acute Pain Management: Scientific Evidence (5th edition), 2020, ANZCA & FPM, Melbourne.

Benson, Transdermal and Topical Drug Delivery Principles and Practice, 2012, John Wiley & Sons.

Panda, Extraction of Capsaicin: Formulation and Evaluation of a Transdermal Patch, 2024, Deep Science Publishing.

* cited by examiner

*Primary Examiner* — Deborah D Carr

(57) ABSTRACT

A transdermal patch and methods for delivering capsaicin to reduce pain are disclosed. The patch comprises capsaicin and a release liner, and may include permeation-enhancing agents. High-dose patches are configured for short-duration application to produce localized defunctionalization of TRPV1-expressing nociceptive terminals, while low-dose patches provide sustained delivery for extended wear. Application to affected dermatomes or regions of sensory loss reduces pain associated with post-herpetic neuralgia, post-surgical neuropathic pain, diabetic neuropathy, radiculopathy, nerve trauma, and bone-related pain states including microarchitectural bone changes. The disclosure further relates to capsaicin compositions, patch structures, and methods of manufacture and use.

9 Claims, No Drawings

METHODS FOR TREATING BONE AND NEUROPATHIC PAIN WITH CAPSAICIN

FIELD OF THE INVENTION

The present invention relates to transdermal drug-delivery systems containing capsaicin and to methods of using those systems for the relief of pain associated with neuropathic pain for example, deafferentation of sensory nerves, including post-herpetic neuralgia (PHN), Post Surgical Pain (PSP) and Chronic Back Pain (CBP).

BACKGROUND OF THE INVENTION

Deafferentation Pain

Deafferentation pain arises when normal sensory input from peripheral nerves to the central nervous system is lost or markedly reduced, leading to ectopic discharges in dorsal-root-ganglion and spinal neurons. Post-herpetic neuralgia (PHN), certain Post Surgical Pain (PSP) and Chronic Back Pain (CBP) are the best-characterized examples. A high-dose, short-wear patch to induce reversible terminal defunctionalization for deafferentation pain. Clinical experience demonstrates a critical and non-interchangeable distinction between high-dose and low-dose capsaicin in the treatment of neuropathic pain, particularly forms involving deafferentation. High-dose capsaicin for example 8 wt % patch produces a concentrated TRPV1-mediated defunctionalization of remaining nociceptor terminals, a mechanism shown to reduce ectopic discharges and dampen dorsal horn hyperexcitability both key drivers of neuropathic and deafferentation pain. The literature consistently reports that only high-dose exposure achieves the threshold level of TRPV1 overstimulation required for this therapeutic effect. In contrast, low-dose capsaicin fails to reach the activation-defunctionalization threshold and therefore produces insufficient TRPV1 desensitization, inadequate suppression of spontaneous firing, and little to no meaningful analgesia in neuropathic pain conditions. Because the therapeutic effect is tightly linked to achieving this high-dose threshold, and because low-dose therapy does not produce comparable anatomical or physiological outcomes, the high-dose range demonstrates clear criticality. Capsaicin exhibits a non-linear, threshold-dependent interaction with TRPV1. Concentrations at or above about 8 wt % generate a supra-threshold calcium influx sufficient to induce terminal depolarization block and reversible defunctionalization. Concentrations below this range activate TRPV1 only partially and fail to produce terminal withdrawal or suppression of ectopic discharges. Because deafferentation pain is maintained by spontaneous ectopic firing in dorsal-root-ganglion and second-order neurons, only supra-threshold capsaicin activation can meaningfully attenuate this pathological mechanism. A person of ordinary skill would not view the high-dose results as predictive of low-dose efficacy, nor consider dose reduction to be a routine optimization, because the mechanism itself shifts once the dose falls below the required TRPV1 activation threshold.

Presently, the symptoms of pain are predominantly treated pharmacologically with systemically active, oral or injectable analgesics and antiphlogistics, alone or in combination and, in part, in combination with psychosomatic or physical therapy, sometimes also in combination with other methods, such as, acupuncture. The last resort for diseases causing neuropathic pain, such as those of the intervertebral disk, is surgery.

An oral analgesic is carried into the patient's circulatory system and prevents the recognition of pain systemically by interrupting the transmission of pain signals from sensory neurons to the pain centers in the brain. Traditional oral analgesics include opioids (narcotics) such as morphine, codeine, methadone, Demerol® (meperidine hydrochloride) or Darvon® (propoxyphene hydrochloride); and non-steroidal anti-inflammatory drugs (NSAIDs), such as aspirin, ibuprofen or naproxen or paracetamol.

The systemic use of these drugs carries patient risk. Opioid use causes a variety of undesired side-effects, including sedation, dizziness, depression, nausea and constipation. Prolonged opioid usage carries a risk of patient addiction. The large and sometimes prolonged doses of non-steroidal anti-inflammatory drugs ("NSAIDs") required to treat intense pain can cause gastric disorders, erosion of the stomach lining and intestinal mucus membrane, nephrotoxicity, hepatotoxicity, as well as internal bleeding. Paracetamol can cause liver toxicity even at lower doses. Orally administered drugs also cause side-affects that restrict physical activity and inhibit effective physical therapy.

In addition, neuropathic pain is often resistant to available drug therapies; a hallmark of neuropathic pain is its intractability. Typical non-steroidal anti-inflammatory drugs (NSAIDs) such as aspirin, indomethacin, and ibuprofen do not relieve neuropathic pain. The neuropathic pain observed in animal models predictive of human clinical outcome does not respond to NSAIDs, opioids or paracetamol. Even effective neuropathic pain treatments can be unpredictable when comparing outcomes across various neuropathic pain types. For example, Uceyler et al. page 76, "High Dose-Capsaicin for the Treatment of Neuropathic Pain: What We Know and What We Need to Know, teaches treatment with capsaicin can be unpredictable when comparing neuropathic pain subtypes, "It is unclear why some patients do respond to Qutenza (8% capsaicin) treatment and others do not".

Unfortunately, all systemic analgesics have a considerable number of undesirable side effects in common. The salicylic acid derivatives and nonsteroidal antiphlogistics are associated considerably and frequently with gastric disorders as a result of the antiproliferative active mechanism. Paracetamol, with a weaker effect, is associated with metabolic stress of liver and kidney functions, especially when used for a prolonged period of time and at required higher doses. Therefore, application of these therapies is limited by the spectrum of undesirable, product-specific effects in each case, because systemic interventions involve all of the organs and the organ systems. In addition, therapies such as surgery, in themselves present significant medical risks to the patient. These pharmacotherapies, do not represent sufficiently tolerable and effective forms of treatment.

Pain can also be treated locally by delivering a TRPV1 receptor agonist directly to the site of pain or in a region near or surrounding the site of pain.

The topical administration of a TRPV1 receptor agonist overcomes some of the drawbacks of painful injections. There is no need for the painfully invasive procedure and professional administration is not needed. The risk of the locally applied anesthetic acting as a systemically administered drug also is much reduced. Dermal patches are well known to administer TRPV1 receptor agonists topically to patients at wound sites and to treat skin ailments. Dermal pain patches have a number of benefits, not the least of which is convenience. For example, capsaicin exhibits, as a pharmacological active mechanism, activate the TRPV1 ion channel, which causes a rapid influx of calcium ion into nociceptive neurons in this manner, the impulse conduction of the nerve path is blocked, which in principle involves all regional nerve fibers.

Given the high incidence of neuropathic pain and its effect on the general population, new innovative remedies are needed to reduce pain in a subject. Advantageous remedies include those that can be applied locally, do not cause negative side-effects, are easy for a patient to apply, do not require painful injections and allow a single administration to treat one or more pain sites for a prolonged period of time.

SUMMARY OF THE INVENTION

High-dose patch about 4%-18% capsaicin: designed for short-duration application about 10-120 min to a defined central dermatome corresponding to deafferentation pain, such as PHN and PSP. This exposure produces reversible TRPV1 long-lasting analgesia following removal.

Traditional central neuropathic pain may arise when a lesion within the brain or spinal cord produces direct deafferentation of central somatosensory pathways, leading to persistent pain despite the absence of ongoing peripheral injury. Such conditions including stroke-related central pain, spinal cord lesions, or demyelinating diseases result from loss or distortion of afferent input to central neurons, which in turn triggers maladaptive sensitization, diminished inhibitory tone, spontaneous firing, and up-regulation of pronociceptive receptor systems. Central neuropathic pain may also arise where an initial peripheral nerve injury evolves into a centrally maintained pain state due to partial or complete deafferentation of sensory pathways. In these conditions, peripheral damage such as viral injury in post-herpetic neuralgia, surgical transection or traction injury, traumatic nerve insult, or root-level compression produces a persistent reduction or distortion of normal sensory input to the spinal dorsal horn. This deafferentation drives a cascade of central changes including dorsal horn hyperexcitability, loss of inhibitory interneuron function, ectopic discharges in second-order neurons, and up-regulation of TRPV1 and other pronociceptive channels on surviving primary afferents and dorsal root ganglion neurons. As the pain state becomes centrally maintained, ongoing neuropathic pain persists even after the original peripheral lesion has healed. High-concentration capsaicin, through selective defunctionalization of TRPV1-expressing nociceptors and reduction of abnormal afferent drive, is therefore well-suited to reduce pain in both traditional central deafferentation pain and centrally maintained deafferentation states arising from initially peripheral injuries.

Central neuropathic back pain can arise from lesions or dysfunction within central sensory pathways without any traumatic injury to the spinal cord itself. Examples include cortical or subcortical stroke involving somatosensory tracts, thalamic pain syndrome, multiple sclerosis plaques affecting spinothalamic pathways, and degenerative neuroinflammatory conditions that disrupt central modulation of nociception. In these patients the peripheral nerves and dorsal roots remain structurally intact, yet pain processing is altered centrally-producing burning, deep aching, pressure-like, or electric qualities that may overlap with peripheral neuropathic phenotypes but arise from fundamentally different neurobiology. Because the underlying mechanisms, sites of pathology, and pharmacologic response patterns differ materially from peripheral neuropathic pain, data obtained in peripheral NP cannot be assumed to predict therapeutic outcomes in central NP.

DETAILED DESCRIPTION OF EMBODIMENTS

High-Dose Patch for Deafferentation Pain

The high-dose embodiment comprises a multilayer patch including:

- a backing film,
- an adhesive matrix containing 6%-12% capsaicin w/w, and
- a removable release liner.

The patch is applied once to skin over the affected dermatome for 5-120 minutes, preferably about 60 minutes, then removed. Following removal, a transient erythema or mild burning subsides within hours while analgesia persists for weeks. The mechanism involves calcium-dependent depolarization and reversible defunctionalization of TRPV1-expressing nociceptive terminals, thereby suppressing ectopic discharges that arise after loss of afferent input. Unlike existing products and methods, this method is optimized for deafferentation pain, not classic neuropathic pain, and can be used in thoracic, cervical, or trigeminal dermatomes affected by PHN, PSP deafferentation, or traumatic nerve loss. Patients with deafferentation pain, including PHN and PSP, are generally considered refractory to topical therapy. Prior literature has repeatedly concluded that topical agents, including capsaicin, fail to provide meaningful relief in this class of pain due to the loss of functional afferent nerve terminals and diminished responsiveness of peripheral nociceptors. For example, as discussed in the research article, "Pharmacotherapy for neuropathic pain in adults: a systematic review and meta-analysis" by Finnerup et al. page 170, "Topical agents have no known relevance for use in central pain, and this is clearly stated in our recommendations." In further evidence, as discussed in the research article, "Post-Herpetic Neuralgia: Pathophysiology and Treatment" by Fields teaches, "Furthermore, it is important to point out that topical preparations are of little use to patients with pure deafferentation form of PHN." page 6. More specifically, topical capsaicin is considered refractory to PHN patients with deafferentation as taught by Fields et al. in "Postherpetic Neuralgia: Irritable nociceptors and Deafferentation" page 220, "In these deafferentation patients, neither heating and capsaicin nor local anesthetic application to the area of maximal pain would affect ongoing and/or allodynia . . . " More recently, Anand et al. "Topical capsaicin for pain management: therapeutic potential and mechanisms of action of the new high-concentration capsaicin 8% patch" page 497 teach that a diagnosis of deafferentation will lead to not being treated with locally acting drugs such as patches, "might inappropriately lead to patients with a diagnosis of de-afferentation to not be treated locally with potentially effective pain medicines." Accordingly, those skilled in the art were taught away from the use of topical capsaicin for deafferentation pain syndromes.

Contrary to these teachings, the inventors have the inventors discovered that supra-threshold TRPV1 activation induces defunctionalization of surviving peripheral terminals that continue to generate ectopic activity. This mechanism was not recognized or suggested in the art and contradicts prior teaching that capsaicin has "no relevance" for central or deafferentation pain. The inventors observed clinically significant pain relief in a patient diagnosed with PHN exhibiting deafferentation-type pain following administration of a topical capsaicin formulation. The observed response of topical capsaicin demonstrated in two deafferentation confirmed patients that, despite the long-held belief that deafferentation pain cannot be effectively managed with topical therapy, residual or alternative mechanisms at the dermal or subdermal interface can be therapeutically modulated by capsaicin. 7 days after therapy both patients exhibited decrease VAS scores. After 14 days patients exhibited increased VAS score reductions averaging a significant 4.5 decrease. These finding are unexpected and provides new evidence that localized peripheral capsaicin interventions can influence pain states previously considered unresponsive to such treatment modalities.

Formulation and Manufacturing Details

The adhesive matrix may comprise acrylic copolymers, polyisobutylene, or silicone elastomers plasticized with fatty-acid esters or glycols to achieve a release rate of 0.05-0.3 μg capsaicin $cm^{-2}$ $h^{-1}$ for the low-dose system. Menthol or other counter-irritants can be pre-solubilized in ethanol or propylene glycol before dispersion. High-dose matrices may be coated from ethanol/toluene blends to ensure uniform capsaicin distribution. Backing films may be polyethylene terephthalate (PET), polyurethane, or aluminized polyester; rate-controlling membranes can include EVA or polyolefin. Patch sizes typically range 5-500 $cm^2$, packaged in foil pouches with removable liners.

EXAMPLES

PHN Thoracic Dermatome Treatment:

An 8% capsaicin patch applied for about 30-60 minutes produced sustained, 4-point VAS pain reduction for about ≥8-12 weeks.

One embodiment reduces pain including neuropathic pain including deafferentation, bone pain, osteoarthritis pain, rheumatoid arthritis (RA), post traumatic arthritis, lupus, juvenile arthritis, psoriatic arthritis (PsA), ankylosing spondylitis, psoriasis, systemic chronic inflammation with fibrosis, back pain, pain from fibromyalgia, pain from muscle strains, pain from muscle sprains or degenerative bone pain or any combination thereof.

In one embodiment, the composition further comprises a treatment enhancing amount of a permeation enhancement agent. In another embodiment, the permeation enhancement agent is menthol. In yet another embodiment, the amount of menthol is 0.5 to 20 wt %. In still another embodiment, the amount of menthol is about 1 to 5 wt %.

In one embodiment of this invention, the therapeutically effective amount of capsaicin is about 8 percent by weight.

In one embodiment, the capsaicin may be a pharmaceutically acceptable base.

In one embodiment, the methods of this invention include reducing pain, including neuropathic pain, deafferentation pain, osteoarthritis pain, rheumatoid arthritis (RA), post traumatic arthritis surgical procedures including: open reduction and internal fixation of fractures; ligament reconstruction such as ACL repair; meniscus repair or meniscectomy; labral or shoulder stabilization surgery; ankle fracture fixation; and joint replacement in advanced post-traumatic degeneration, lupus, juvenile arthritis, psoriatic arthritis (PsA), ankylosing spondylitis, psoriasis, systemic chronic inflammation with fibrosis, back pain, pain from fibromyalgia, pain from muscle strains, pain from muscle sprains or bone pain or any combination thereof, in a subject comprising applying on a skin surface of the subject at or near the site of pain, a patch comprising a composition comprising a therapeutically effective amount of capsaicin, wherein the amount of capsaicin is less than about 8 percent by weight, and wherein application of the patch provides transdermal delivery of an amount of capsaicin sufficient to reduce the pain in the subject.

In one embodiment, the patch is applied for about 8 to 12 hours.

In one embodiment, methods of this invention provide that application of a patch of this invention reduces neuropathic pain including deafferentation pain, bone pain, back pain, diabetic neuropathic pain, nerve compression or nerve trauma, or any combination.

In one embodiment, methods of this invention include compositions further comprising a treatment enhancing amount of a permeation enhancement agent. In one embodiment, methods include the use of menthol as a permeation enhancement agent. In one embodiment, the amount of method used in a method of this invention is 0.5 to 20 percent by weight. In one embodiment the amount of menthol used in a method is between about 1 to 5 percent by weight.

In one embodiment, the methods of this invention employ a therapeutically effective amount of capsaicin, wherein that amount is about 1 and about 8 percent by weight.

In one embodiment of the invention, the capsaicin employed in a method of this invention is its pharmaceutically acceptable salt, free base or any combination thereof. In another embodiment of the invention, the capsaicin employed in a method of this invention is its pharmaceutically acceptable free base.

In one embodiment, methods of this invention reduce pain within about 12 hours of administration. In one embodiment, methods of this invention reduce pain within about 24 hours of administration. In one embodiment, methods of this invention reduce pain within about 48 hours of administration. In one embodiment, methods of this invention reduce pain within about 1 week of administration. In one embodiment, methods of this invention reduce pain within about 2 weeks of administration. In one embodiment, methods of this invention reduce pain within about 1 month of administration.

In one embodiment, methods reduce pain about 3 months. In yet another embodiment, methods reduce pain for more than about 6 months. In yet another embodiment, methods reduce pain for more than about one year.

In some embodiments, methods of this invention include an additional step for enhanced delivery of said capsaicin. In one embodiment, methods include the use of iontophoresis, a battery powered electronic stimulant or magnetophoresis for enhanced deliver of an active ingredient, e.g., capsaicin.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The present invention is directed to a patch for transdermal delivery of capsaicin for reducing pain, including neuropathic pain, for example; deafferentation pain, bone pain, Diabetic Peripheral Neuropathy (DPN), Postherpetic Neuralgia (PHN), Lumbar or Cervical Radiculopathy (sciatica/nerve-root compression), Trigeminal Neuralgia, Central Post-Stroke Pain, Multiple Sclerosis-Related Neuropathic Pain, Chemotherapy-Induced Peripheral Neuropathy (CIPN), HIV-Associated Neuropathy, Spinal Cord Injury and Related Neuropathic Pain, Carpal Tunnel Syndrome (median nerve entrapment), Post-Surgical Neuropathic Pain or any combination thereof, comprising a composition comprising a therapeutically effective dosage of capsaicin and methods of use thereof.

Non-limiting examples of post-surgical pains and procedures which cause neuropathic deafferentation pain include; traumatic nerve injury, for example amputation, digital nerve transection, limb nerve laceration; post-surgical neuropathic pain, for intercostal nerve injury, inguinal hernia ilioinguinal/iliohypogastric nerve injury, saphenous nerve injury after knee surgery; radiculopathy with sensory loss; for example herniated disc, foraminal stenosis compressing/damaging the dorsal root; peripheral nerve avulsion injuries, for example brachial plexus root avulsion; advanced diabetic peripheral neuropathy, especially late-stage axonal loss with sensory deafferentation; chemotherapy-induced neuropathy with axonal degeneration, for example paclitaxel, oxaliplatin, vincristine; severe chronic entrapment neuropathies, for example end-stage carpal tunnel, severe ulnar neuropathy at elbow, advanced tarsal tunnel; Shoulder surgery, for example rotator cuff repair, labral repair; hip surgery, for example arthroscopy, fracture fixation, hip replacement; spine surgery, for example laminectomy, discectomy, fusion; elbow surgery, for example ulnar nerve transposition, fracture fixation, arthroscopy; foot and toe surgeries, for example bunionectomy, hammertoe repair, Morton neuroma excision; sinus and nasal surgeries, for example septoplasty, turbinate reduction, endoscopic sinus surgery; thyroidectomy or parathyroid surgery; parotidectomy and other salivary gland surgeries; mandibular and maxillofacial surgeries, for example dental implants, wisdom tooth extraction, orthognathic surgery; vascular bypass surgeries, for example femoral, popliteal, or radial artery harvest; mastectomy flap revision or reconstruction procedures; non-inguinal hernia repairs, for example femoral, umbilical, ventral, or epigastric; prostatectomy; penile or scrotal surgeries, for example dorsal penile nerve or perineal branch injury.

The patch of the present invention may be used to reduce neuropathic pain, including deafferentation. The present invention may be used to reduce pain for extended time periods, e.g., weeks or months. The patch and methods of use thereof according to the present invention may be better understood with reference to the drawing and accompanying descriptions.

Before explaining at least one embodiment of the present invention in detail, it is to be understood that the invention is not limited in its application to the details of construction and the arrangement of the components as set forth in the following description or illustrated in the drawing. The invention is capable of other embodiments or of being practiced or carried out in various ways. Also, it is to be understood that the phraseology and terminology employed herein are for the purpose of description and should not be regarded as limiting.

I. Definitions

As used herein, the term "patch" refers to a medicated patch, e.g., a patch, comprising a composition comprising at least one active ingredient that is placed on the skin to deliver a continuous dosage of the active ingredient through the skin and into the surrounding tissue. In one embodiment, the active ingredient may penetrate deeply below the skin to a site of pain for deep tissue pain relief. In one embodiment, the active ingredient penetrates just below the skin to a site of pain localized therein for local pain relief. In one embodiment, the continuous dosage of the active ingredient provides minimal entry of the active ingredient into the blood stream. In another embodiment, the continuous dosage provides no entry of the active ingredient into the blood stream.

As used herein, the term "patch" may also be referred to herein as a "topical delivery system", a "topical patch delivery system", an "adhesive patch", a "transdermal patch", a "transdermal delivery system", an "analgesic patch", a "topical carrier system".

Transdermal patches are a well-accepted technology used to deliver a wide variety of pharmaceuticals. Patches of the present invention may be placed on the skin for specified therapeutic time periods and remain in place for up to about 30 minutes, or up to about 1 hour, or up to about 2 hours, or up to about 12 hours or up to about 24 hours.

Patches may comprise an adhesive to remain in place when placed on the skin or may be adhered by other means including adhesive tape or strips. In addition, patches of the present invention may be perforated and/or stretchable in order that they may be wrapped around an appendage or body part. In certain embodiments, a stretchable patch may be wrapped fully around an appendage or body part. In alternative embodiments, a stretchable patch may be wrapped partly around an appendage or body part. For example, a patch of the present invention may be wrapped around a knee, ankle, leg, elbow, wrist, finger, arm or neck. By wrapping the patch, pain relief may be provided at sites recalcitrant to a patch that would otherwise be expected to remain in place using just an adhesive, for example a moving joint such as an elbow, knee or wrist joint.

In one embodiment, the patch is an adhesive patch. In another embodiment, the patch is not adhesive. In yet another embodiment, the patch may be wrapped around a bodily appendage. In still another embodiment, the patch may be both adhesive and able to be wrapped around an appendage.

Conventional dermal patches include a carrier that holds a drug and allows the drug to be released onto a patient's skin for absorption. Many different kinds of dermal patches are known, including matrix type patches, reservoir-type patches, multi-laminate drug-in-adhesive type patches, and monolithic drug-in-adhesive type patches, and many others. Such patches can be readily prepared using technology which is known in the art such as described in Remington's Pharmaceutical Sciences, 18th or 19th editions, published by the Mack Publishing Company of Easton, Pa and Remington Essentials of Pharmaceutics, Linda B Felton, Pharmaceutical Press 2012, ISBN 978 0 85711105 0, both of which are fully incorporated by reference.

Patches of the present invention may include: (1) a backing layer, having an adhesive thereon; (2) an analgesic component for delivery of the analgesic, preferably, an analgesic in a carrier, referred to herein as an "analgesic composition" or "composition"; wherein the analgesic components are collectively referred to herein as the "active components" or "active ingredients". These components are described in more detail below. In another embodiment, the analgesic composition comprises capsaicin.

Patches of the present invention can be used on any body part and in any shape or size or can be customized to fit irregularly shaped body parts associated with pain, e.g., joints, back, neck, arms, legs, shoulders, hips, wrists, ankles, head, face, knees and/or fingers. For example, patches of the invention can be rectangular, square, round or oval in shape. Patches may also be perforated and stretchable for wrapping around different body appendages and/or joints, e.g., arms, legs, wrists, ankles, knees and/or fingers. Varying the size of the patch used varies the dosage. Often a patch is cut and only a portion is used. In some instances, the use of more than one patch may be advisable.

In one embodiment, patches are 20 cm×14 cm. In another embodiment, patches are smaller than 20 cm×14 cm. In yet another embodiment, patches are larger than 20 cm×14 cm. In one embodiment, patches are cut to the size and shape needed for use in pain reduction. In one embodiment, the patch remains intact while the size of the patch changes upon stretching.

Patches suitable for use in the present invention include, but are not limited to, (1) the matrix patch; (2) the reservoir patch; (3) the multi-laminate drug-in-adhesive patch; and (4) the monolithic drug-in-adhesive patch; as described in "Dermal Drug Delivery: From Innovation to Production" (Tapash K. Ghosh et al. eds., first edition, Jan. 21, 2020, ISBN-13 978-1466582712), hereby incorporated in full herein by reference and specific information disclosed that is usable in this invention is not limited to those disclosed specifically with capsaicin. These patches are well known in the art and generally available commercially.

The matrix patch comprises a drug containing matrix, an adhesive backing film overlay, and preferably, a release liner. In some cases, it may be necessary to include an impermeable layer to minimize drug migration into the backing film (e.g., U.S. Pat. No. 4,336,243, incorporated in full herein by reference). The drug-containing matrix is held against the skin by the adhesive overlay. Examples of suitable matrix materials include, but are not limited to, lipophilic polymers, such as polyvinyl chloride, polydimethylsiloxane, and hydrophilic polymers like polyvinylpyrrolidone, polyvinyl alcohol, hydrogels based on gelatin, or polyvinylpyrrolidone/polyethylene oxide mixtures.

The reservoir type patch design is characterized by a backing film coated with an adhesive and a reservoir compartment comprising a drug formulation, preferably in the form of a solution or suspension that is separated from the skin by a semipermeable membrane (e.g., U.S. Pat. No. 4,615,699, hereby incorporated in full herein by reference). The adhesive coated backing layer extends around the reservoir's boundaries to provide a concentric seal with the skin and hold the reservoir adjacent to the skin.

The monolithic/single drug-in-adhesive patch design is characterized by the inclusion of the drug formulation in the skin contacting adhesive layer, a backing film, and preferably, a release liner. The adhesive functions both to release the analgesic and adhere the analgesic matrix to the skin. The drug-in-adhesive system does not require an adhesive overlay and thus the patch size is minimized. Also, drug-in-adhesive type patches are thin and comfortable (e.g., U.S. Pat. No. 4,751,087, incorporated in full herein by reference).

The multi-laminate drug-in-adhesive patch design further incorporates an additional semi-permeable membrane between two distinct drug-in-adhesive layers or multiple drug-in-adhesive layers under a single backing film. See Peterson, T. A. and Dreyer, S. J. 21 Proceed. Intern. Symp. Control. Rel. Bioact. Mater. 477-478 (Nice, France 1994), hereby incorporated in full herein by reference).

The backing layer or backing serves as the upper surface of the patch and functions as the primary structural element and provides the patch with its flexibility. The material selected for the backing material should be selected so that it is substantially impermeable to the local analgesic and any other materials present; the backing is preferably made of a sheet or film of a flexible elastomeric material. The backing supports the active layers by way of an adhesive and holds the active layers against the application site. The combination of backing and adhesive should be biocompatible, non-irritating to the skin, breathable and able to hold the patch firmly against the skin.

In an embodiment of the invention the capsaicin patch is non-aqueous. Aqueous based capsaicin patches have poor adhesive properties and fall off easily because the vaporization of moisture can problematically cause changes in adhesion and physical properties. Moreover, due to very little adhesion, aqueous base patches are difficult to be attached to the skin for a long period of time. Aqueous base patches have thick plasters because they contain moisture; therefore, aqueous base patches are poorly compatible with the skin. Aqueous base patches are not stretchable. In certain embodiments of the invention the patch is stretchable.

It is difficult to ensure sufficient amount of capsaicin is permeated through the skin and into the body with aqueous based patches. In certain embodiments of the invention, capsaicin permeates through the skin onto the muscles, bones, fluids; including the synovial fluid. In other embodiments capsaicin permeates into the systemic circulation.

Nonaqueous patches have poor permeability into and through the skin because the capsaicin is not dissolved and is present in a crystalline state. High concentrations maybe required which could lead to undesirable side effects.

As a softener, polybutene or liquid paraffin also known as mineral oil may be added to a non-aqueous patch. If comprised of block copolymer or silicone, adding liquid paraffin provides good plaster. The liquid paraffin has compatibility to isoprene groups of the styrene-isoprene-styrene block copolymer, and it can make plaster. The swelling and soft nature so said plaster have elastic force when applied as a skin patch. The composition amount of liquid paraffin is usually about double to composition amount of styrene-isoprene-styrene block copolymer.

Backings for use in patches of the invention are preferably made of a flexible, biocompatible material that imitates the elastic properties of skin and conforms to the skin during movement. Preferred have a moisture-vapor transmission rate similar to human skin. This reduces the chance of an infection developing under the patch after it is applied.

Preferably, the backing layer is derived from synthetic polymers like polyolefin oils polyester, polyethylene, polyvinylidene chloride, and polyurethane or from natural materials like cotton, wool, etc. Non-occlusive backings allow the area to breathe (i.e., promote water vapor transmission from the skin surface). In one embodiment, the backing film is an occlusive polyolefin foil (Alevo, Dreieich, Germany). The polyolefin foil is preferably about 0.6 to about 1 mm thick. Other suitable backings are commercially available; for example, suitable backings can be purchased from 3M (St. Paul, Minn.).

In one embodiment, the patch includes an occlusive dressing. In another embodiment, the patch includes a non-occlusive dressing. For example, a non-occlusive patch can enable moisture vapor on the surface of the skin to evaporate through the patch so as to prevent the undesired accumulation of moisture which, if it occurred, could cause the patch to fall off or even facilitate the growth of bacteria beneath the patch.

Permeable membranes can be used with patches of the present invention to overlay the portion of the patch adjacent to the skin to permit delivery of the patch's active ingredients to the application site. Preferably, the permeable membrane comprises a breathable material that is agreeable to the surface of a surgically closed wound and permits local delivery of local anesthetic into the skin of the patient at the wound site. Permeable membranes permit controlled delivery of the active components of the patch.

Permeable membranes useful in the present invention include thin non-porous ethylene vinyl acetate films or thin micro-porous films of polyethylene and polypropylene. Preferably, the permeable membrane is an ethyl vinyl acetate copolymer membrane. Suitable permeable membranes are commercially available; for example, suitable permeable membranes can be purchased from 3M (St. Paul, Minn.).

Adhesives may be used with patches of the present invention to adhere the active components to the backing and to adhere the backing to the patient's application site. Preferably, adhesives useful in the present invention can function under a wide range of conditions, such as, high and low humidity, bathing, sweating etc. Adhesives for use with patches of the present invention are well known in the art and selection is readily accomplished by an ordinary practitioner. Suitable adhesives include, but are not limited to, polyisobutylene-based adhesives, silicone-based adhesives, and acrylic-based adhesives. Preferably the adhesive is a composition based on natural or synthetic rubber; a polyacrylate such as, polybutylacrylate, polymethylacrylate, poly-2-ethylhexyl acrylate; polyvinylacetate; polydimethylsiloxane; and hydrogels (e.g., high molecular weight polyvinylpyrrolidone and oligomeric polyethylene oxide).

Patches of the present invention deliver their medicine directly to the site of a person's pain. This may eliminate some of the side effects that come with oral dosing or local injections. For instance, some analgesics are likely to cause an upset stomach unless they're taken with food. And, because patches of the present invention provide minimal release of their active ingredient into the blood stream and provide release of their active ingredient slowly into the body tissues through the skin, people should also get more consistent pain relief than they do with oral dosing or injections.

The composition of the present invention is a pharmaceutical composition. The pharmaceutical composition of the invention includes a pharmaceutically acceptable carrier.

As used herein, the terms "pharmaceutically acceptable carrier", "carrier", or "vehicle" refers to carrier materials suitable for transdermal drug administration. Carriers and vehicles useful herein include any such materials known in the art which are nontoxic and do not interact with other components. As used herein the term "a pharmaceutically acceptable carrier" refers to any substantially non-toxic carrier conventionally useable for transdermal administration of pharmaceuticals in which an active ingredient will remain stable and bioavailable. In one embodiment of the present invention, the local-analgesic of the composition of the present invention comprises a pharmaceutically acceptable carrier to contain and deliver the active component to the application site. As used herein, the term "carrier" may herein be interchangeable with the term "patch"

In certain embodiments, carriers are sterile and pharmaceutically acceptable for topical application and delivery of an active ingredient into or through a patient's skin. Preferred functional characteristics of carriers are low adhesive strength, breathability, and conformability to the application area.

Pharmaceutically acceptable carriers for use in the invention are standard in the art, for example, matrix-type carriers, reservoir-type carriers, multi-laminate-type carriers, and monolithic drug-in-adhesive type carriers, such as those disclosed in "Dermal Drug Delivery: From Innovation to Production" (Tapash K. Ghosh et al. eds., first edition, Jan. 21, 2020, ISBN-13 978-1466582712); see also Kristine Knutson and Lynn K. Pershing, Topical Drugs, in Remington: The Science And Practice Of Pharmacy 866-885 (Alfonso R. Gennaro ed., 1995), Remington Essentials of Pharmaceutics, Linda B Felton, Pharmaceutical Press 2012, ISBN 978 0 85711105), all of which are fully incorporated by reference and specific carriers disclosed that are usable in this invention are not limited to those disclosed specifically with capsaicin.

In an embodiment, the carrier is a matrix-type drug carrier. Matrix-type drug carriers are well known in the art. Suitable matrix-type drug carriers include, but are not limited to, the adhesives discussed below, such as polyisobutylene-based adhesives, silicone-based adhesives, and acrylic-based adhesives.

In another embodiment, the carrier is a hydrogel. Hydrogels are a mixture of water and a gelling agent, such as a hydrophilic polymer. In general, hydrogels form a three-dimensional lattice of polymer chains that retains an aqueous solution in a flexible, stable shape. Preferred hydrogels contain gelling agents distributed substantially uniformly throughout the carrier liquid, which is typically aqueous and may contain an alcohol and/or an oil.

Preferred gelling agents include, but are not limited to, crosslinked acrylic acid polymers such as carboxypolyalkylenes; hydrophilic polymers such as polyethylene oxides, polyoxyethylene-polyoxypropylene copolymers and polyvinyl alcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

Suitable hydrogels are commercially available, for example, suitable hydrogels can be purchased from BASF (St. Paul, Minn.) or Noveon (Cleveland, Ohio). In yet another embodiment, the carrier is not a hydrogel, nor does it contain water which increases adherence to the subject.

As used herein, the term "active ingredient" refers to a suitable drug that provides local analgesia or deep tissue analgesia, or a combination thereof, or a drug that provides a regional blockage of nervous pathways that carry pain signals. As used herein, the term "active ingredient" may also be referred to as hot melting.

As used herein, the term "analgesia" refers to a neurological or pharmacological state characterized by an absence of normal sensibility to pain, without an effect on consciousness. Accordingly, painful stimuli are either not perceived at all, or they are moderated such that, even though they may still be perceived, they are no longer painful.

In one embodiment, an active ingredient may act as an analgesic. The analgesic may operate as a local analgesic and/or penetrate deeper and enter the blood stream. In one embodiment, the active ingredient functions as a local analgesic. In another embodiment, the active ingredient functions as an analgesic for deeper tissue. In yet another embodiment, the active ingredient does not enter the blood stream. In another embodiment, the active ingredient only minimally enters the blood stream.

In one embodiment, administration of a patch comprising a composition comprising the active ingredient, acts to reduce pain, including neuropathic pain, deafferentation pain, bone pain, osteoarthritis pain, rheumatoid arthritis (RA), post traumatic arthritis, lupus, juvenile arthritis, psoriatic arthritis (PsA), ankylosing spondylitis, psoriasis, systemic chronic inflammation with fibrosis, back pain, pain from muscle strains, pain from muscle sprains or bone degeneration pain or any combination thereof, in a subject.

As used herein, the term "reducing pain" refers to alleviating pain localized at a site of interest. The reduction of pain may include alleviating pain in an area around the site of interest.

As used herein, "pain," includes both acute pain and chronic pain, which may be centralized pain, peripheral pain, or combination thereof.

As used herein, the term "acute pain" refers to centralized or peripheral pain that is intense, localized, sharp, or stinging, and/or dull, aching, diffuse, or burning in nature and that occurs for short periods of time. Acute pain can last for less than 7 days, less than about 30 days, less than about 60 days, less than about 90 days, or less than about one year.

As used herein, the term "chronic pain" refers to centralized or peripheral pain that is intense, localized, sharp, or stinging, and/or dull, aching, diffuse, or burning in nature and that occurs for extended periods of time (i.e., persistent and/or regularly reoccurring).

As used herein, the term "neuropathic pain" refers to any and all types of neuropathic pain regardless of the cause including pain from deafferentation. Neuropathic pain refers to pain that originates from pathology of the nervous system. Neuropathic pain reflects both peripheral and central sensitization mechanisms. Abnormal signals arise not only from injured axons but also from the intact nociceptors that share the innervation territory of the injured nerve. Neuropathic pain may result from lesions of the central nervous system, or from the peripheral nervous system. Neuropathic pain may also arise from disorders of ion channels, such as the sodium channels. The nervous system can generate and perpetuate pain (i.e., neuropathic), without any ongoing stimuli from injury. Neuropathic pain is often puzzling and frustrating for both patients and physicians because it seems to have no cause, responds poorly to standard pain therapies, can last indefinitely and even escalate over time, and often results in severe disability. The reduction of neuropathic pain as described herein refers to the alleviation or elimination of the neuropathic pain associated with a neuropathy.

Four pathological mechanisms are associated with the generation of pain in peripheral tissues in neuropathic pain conditions. These are: 1) nociceptor sensitization, whereby nociceptors have enhanced sensitivity to stimuli; 2) spontaneous activity related either to abnormal activity of transduction channels, or abnormal sensitivity of spike generation mechanisms; 3) abnormal coupling between sympathetic efferent fibers and nociceptors (sympathetically maintained pain); and 4) deafferentation (complete or partial), a central mechanism of pain whereby pain results from abnormal activity in neurons concerned with pain in the central nervous system as a result of altered input from primary afferents. Capsaicin is effective in these centrally maintained deafferentation states because defunctionalization of TRPV1-expressing nociceptors reduces the abnormal residual afferent input that continues to drive central sensitization, thereby interrupting the very mechanism that sustains the chronic pain.

The primary sensory neurons that carry signals related to pain are called C-fiber and A-delta nociceptors. Normally, they fire action potentials in response to noxious mechanical, thermal, and/or chemical stimuli. Lumbar disk herniation with its accompanying chemical irritants to the adjacent nerve root can produce sciatic nerve pain. Carpal tunnel syndrome is due to a combination of repetitive stretching of the median nerve, compression caused by edema and hypertrophy of surrounding tissues, and inflammation producing chemical irritation of the median nerve. Trigeminal neuralgia has been attributed to vascular compression on the trigeminal nerve near the brain stem and may also relate to conditions such as multiple sclerosis.

Nerve fibers that have been damaged by injury or disease can fire spontaneously at the site of injury or at ectopic foci along the damaged nerve. Resulting paroxysms of pain are often described as lancinating, stabbing, or shooting. It is believed that when many nerve fibers are affected and fire asynchronously, neuropathic pain has a quality of continuous burning results. In addition, however, the nerve fibers that share the innervation territory of the injured nerve can also discharge abnormally. This discharge arises in the skin and therefore lends itself to topical therapy. Clonidine applied topically has been discovered to relieve pain after delivery to the painful site, for example.

Under normal conditions, sensations are transmitted from peripheral tissues via a connected chain of neurons in the spinal cord, brain stem, and brain. Interruption of any portion of that chain provides the potential for increased irritability and firing of nerves further up the pathway. This phenomenon explains how phantom limb pain can occur: Loss of sensory input from a limb can produce spontaneous firing of second- and third-order neurons, resulting in pain and other sensory experiences in the missing limb. Similarly, nerves damaged by diabetic neuropathy, post-herpetic neuropathy, or peripheral nerve trauma may generate firing in the higher-order nerves and, thus, ongoing pain.

Examples of specific sources of neuropathic pain for which the methods of the present invention can be used include autoimmune diseases, e.g., multiple sclerosis; metabolic diseases, e.g., diabetic neuropathies; back pain, spine or back surgery; postherpetic neuralgia; vascular disease; trauma; complex regional pain syndrome type II (CRPS-II); carpal tunnel syndrome; phantom limb pain; chemotherapy-induced neuropathy; central pain syndrome; trigeminal neuralgia; reflex sympathetic dystrophy syndrome; nerve compression; stroke; spinal cord injury; or HIV sensory neuropathy, or other nerve pain disorders having a predominantly neurological cause.

In contrast to feelings of immediate pain upon tissue injury, neuropathic pain can develop days or months after a traumatic injury. Furthermore, while pain caused by tissue injury is usually limited in duration to the period of tissue repair, neuropathic pain frequently is long lasting or chronic. Moreover, neuropathic pain can occur spontaneously or as a result of stimulation that normally is not painful.

Traumatic injury to a joint or weight-bearing structure commonly produces a dual pain phenotype arising from both microarchitectural bone changes and disruption of sensory afferent input. Mechanical forces sufficient to generate subchondral bone marrow edema, trabecular microdamage, cortical microfracture, periosteal irritation, or subchondral remodeling frequently occur in parallel with traction, compression, or partial transection of peripheral sensory nerve branches serving the same anatomical region. As a result, patients often present with a combination of nociceptive bone pain generated by microarchitectural bone lesions and neuropathic pain features arising from localized deafferentation, including sensory loss, paresthesias, burning pain, or the characteristic numb-yet-painful presentation. These overlapping pain states are typical of post-traumatic arthritis, post-surgical orthopedic conditions, and ligamentous or osteochondral injuries involving the knee, hip, ankle, shoulder, spine, and other musculoskeletal structures.

The invention encompasses treatment of pain arising from microarchitectural bone changes as well as pain having a deafferentation component. These categories are not mutually exclusive; rather, traumatic and post-surgical conditions frequently exhibit both structural bone pathology and partial loss of sensory input. Bone marrow lesions, trabecular microfractures, and periosteal irritation generate sustained nociceptive signaling through TRPV1-expressing afferents, while concurrent nerve traction, contusion, or transection results in localized deafferentation and neuropathic pain. The disclosed capsaicin patches are configured to target both pathways by modulating TRPV1 activity within dermatomes or anatomical regions corresponding to the affected bone and injured sensory nerves and can be administered with or without other remedies. The formulations, dosage strategies, and application methods described herein are therefore applicable to a genus of pain states in which microarchitectural bone injury and sensory deafferentation coexist or contribute independently to patient symptoms.

In certain embodiments, methods are provided for treating pain associated with microarchitectural bone changes, deafferentation neuropathic pain, or a combination thereof, by topically applying a capsaicin patch to the skin overlying or adjacent to the anatomical region of pain. High-dose patches may be applied for a short duration to induce reversible defunctionalization of TRPV1-expressing nociceptive terminals and to reduce both nociceptive and deafferentation-related input. Low-dose patches may be used for extended wear to provide sustained localized delivery of capsaicin and continuous modulation of TRPV1 signaling. The patch may be placed to correspond with affected dermatomes, zones of sensory loss, or regions associated with underlying bone marrow edema, trabecular microdamage, or periosteal irritation. Such methods provide localized analgesia and are suitable for treating mixed pain phenotypes arising in for example post-traumatic, post-surgical, degenerative, or inflammatory musculoskeletal conditions.

Microarchitectural bone change patients can often identify pain arising from micro-architectural bone changes (MABC) based on a recognizable pattern of symptoms that differs from muscle, joint, or nerve-root pain. Individuals commonly report a deep, internal ache that is difficult to localize with a fingertip and instead is described as "inside the bone" or "beneath the surface." The pain often worsens with weight-bearing or impact-based activities such as standing, walking, stair climbing, or lifting, yet improves at rest. Many patients also notice that pressing on the area does not reproduce the pain, distinguishing it from muscle or tendon disorders. Morning stiffness, sensitivity to vibration (such as riding in a car), and pain that increases after prolonged activity are additional clues. When these features cluster together deep diffuse ache, loading sensitivity, minimal tenderness to touch, and worsening with impact patients and clinicians can reasonably suspect that the source may be micro-architectural deterioration rather than soft-tissue or peripheral nerve origin.

As used herein, the term "osteoarthritis pain" refers to pain associated with a degenerative joint disease where the cartilage that normally cushions the joint and protects it from impact erodes.

As used herein, the term "pain from fibromyalgia" refers to pain associated with a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism.

As used herein, the term "back pain" refers to pain associated with all regions of the back including lower, mid and upper back pain. Back pain can be nociceptive or neurologic or the combination of both.

As used herein, the term "bone pain" refers to pain associated with conditions leading to degenerative bone disorders characterized by low bone mass and microarchitectural deterioration of bone tissue, leading to enhanced bone fragility and increased fracture risk. Additionally, microarchitectural changes are not deteriorating but rather the bone remodeling increases bone density which leads to bone pain.

As used herein, the term "pain from muscle strains" refers to pain associated with muscle tears and/or pulled muscles. Muscle strains occur when an excessive amount of force or pressure is directed onto muscles that cause damage or tearing to the muscle fibers and/or surrounding tendons. common muscle strains, torn muscles and pulled muscles are: Achilles tendon tear, pulled backs, lower back muscle strain, tearing the rotator cuff, abs (abdominal) muscle strains, calf muscle strain, hamstring muscle strain, quads (quadriceps) muscle strain, leg muscle strain, knee (or plantaris) muscle strain, chest muscle strain, groin pull or muscle strain, bicep muscle strain, and arm muscle strain.

As used herein, the term "pain from muscle sprains" refers to pain associated with a stretch or tear of a ligament, the band of connective tissues that joins the end of one bone with another. Sprains are caused by trauma such as a fall or blow to the body that knocks a joint out of position and, in the worst case, ruptures the supporting ligaments.

The patches of the present invention can be used to reduce pain such as neuropathic pain for example deafferentation pain or bone pain. For example, the patches of the present invention may be used to reduce pain associated with diabetic neuropathy, back pain, carpel tunnel syndrome or other pains associated with nerve injury or any combination thereof. In addition, the patches of the present invention may also be used to reduce pain associated with fibromyalgia, muscle strains, muscle sprains, arthritis including osteoarthritis, rheumatoid arthritis (RA), post traumatic arthritis, lupus, juvenile arthritis, psoriatic arthritis (PsA), ankylosing spondylitis, psoriasis or systemic chronic inflammation with fibrosis or bone degeneration or any combination thereof.

Compositions of this invention are described below. In some embodiments, any of the compositions of this invention will comprise capsaicin, in any form or embodiment as described herein. In some embodiments, any of the compositions of this invention will comprise a combination of capsaicin and menthol, in any form or embodiment as described herein. In some embodiments, any of the compositions of this invention will consist of capsaicin, in any form or embodiment as described herein. In some embodiments, any of the compositions of this invention will consist of a combination of capsaicin and menthol, in any form or embodiment as described herein. In some embodiments, any of the compositions of this invention will consist essentially of capsaicin, in any form or embodiment as described herein. In some embodiments, any of the compositions of this invention will consist essentially of a combination of capsaicin and menthol, in any form or embodiment as described herein. The term "comprise" refers to the inclusion of the indicated active agents, such as a combination of capsaicin and menthol, as well as inclusion of other active agents, and pharmaceutically acceptable carriers, excipients, emollients, stabilizers, etc., as are known in the pharmaceutical industry. The term "consisting essentially of" refers to a composition, whose only active ingredients are the indicated active ingredients, however, other compounds may be included which are for stabilizing, preserving, etc. the formulation, but are not involved directly in the therapeutic effect of the indicated active ingredients. The term "consisting essentially of" may refer to components which facilitate the release of the active ingredients. The term "consisting" refers to a composition, which contains the active ingredient and a pharmaceutically acceptable carrier or excipient.

As used herein, the term "transdermal delivery" refers to the delivery of a compound, e.g., an active ingredient of this invention or other therapeutic agent, through one or more layers of the skin (e.g., epidermis, dermis, etc). Transdermal delivery of an active ingredient of this invention, e.g., capsaicin, may include administration of the active ingredient to the skin surface of a subject, including a human subject, so that the active ingredient passes through the skin tissue and, for example, into deeper tissue thereby providing deep tissue relief of pain.

Administration of the active ingredient or compositions of this invention includes topical administration. As used herein, the term "topical" refers to administration of a patch of this invention at the point of application. The phrase "topically applying" describes application onto one or more surfaces(s) including epithelial surfaces. Ideally, the substance will not reside in the skin for any extended period of time, but will penetrate into localized tissue, deep tissue and/or synovial fluids in order to provide localized, deep tissue or "joint" pain relief or any combination thereof. In one embodiment, transdermal delivery is enhanced, wherein enhancement may be through chemical or physical means.

As used herein, the term "therapeutically effective amount" refers to that amount of any active ingredient, e.g., capsaicin, which provides a therapeutic or beneficial effect for a given condition and administration regimen to a subject. The concentration of the substance is selected so as to exert its pharmaceutical effect at dosages. In certain circumstance, such dosages are low enough to avoid significant side effects to a subject. The effective amount of an active ingredient may vary with the particular site at which a patch of this invention is placed, e.g., the thickness of the skin tissue at the treatment site, the age and physical condition of the biological subject being treated, the severity of the condition, the duration of the treatment, the nature of concurrent therapy, the specific compound, composition or other active ingredient employed, the particular carrier utilized, and like factors. The effective amount of any of the active ingredients comprised in the compositions of the present invention may, for example, be the amount that results in a therapeutic or beneficial effect following its administration to a subject. The concentration of an active ingredient is selected so as to exert its pharmaceutical effect, but low enough to avoid significant side effects within the scope and sound judgment of the skilled artisan. The effective amount of the composition may vary with the particular epithelial tissue being treated, the age and physical condition of the biological subject being treated, the severity of the condition, the duration of the treatment, the nature of concurrent therapy, the specific compound, composition or other active ingredient employed, the particular carrier utilized, and like factors. As used herein, the term "therapeutically effective amount" may also be referred to herein as a "pharmaceutically effective amount".

As used herein, the term "permeation enhancement" refers to enhancement of the percutaneous penetration of the active ingredient, allowing for a fast onset of action. As used herein, the term "permeation enhancement" may also be referred to as "transdermal enhancement" or "penetration enhancement". In one embodiment, permeation enhancement may be performed through the use of chemical permeation enhancers. In another embodiment, permeation enhancement may be performed through the use of physical permeation enhancers. Physical permeation enhancer techniques include magnetophoresis, iontophoresis or a battery powered electronic stimulant.

Iontophoresis, also known as Electromotive Drug Administration (EMDA), is a technique using a small electric charge to deliver a medicine, drug, active ingredient or other chemical through the skin. It may function similar to an injection without the needle, for example EMDA may be used for localized entry of a drug into the skin. In addition, EMDA may be used for concentrated application of a medication under the skin (FIG. 2). As used herein, "iontophoresis" refers to a non-invasive method of propelling high concentrations of a charged substance, for example a medication, a drug, an active ingredient or a bioactive agent, transdermally by repulsive electromotive force using a small electrical charge applied to an iontophoretic chamber containing a similarly charged active agent and its vehicle. One or two chambers may be filled with a solution containing an active ingredient and its solvent, also called the vehicle. The positively charged chamber, called the anode, will repel a positively charged chemical, whereas the negatively charged chamber, called the cathode, will repel negatively charged chemicals into the skin.

Iontophoresis is well known for use in transdermal drug delivery. Unlike transdermal patches, this method relies on active transportation within an electric field. In the presence of an electric field electromigration and electroosmosis are the dominant forces in mass transport. These movements are measured in units of chemical flux, commonly μmol/cm2 h. As described herein, iontophoresis may be used in conjunction with a patch of this invention for "permeation enhancement" of an active ingredient.

At the same time, the active ingredient must not penetrate so effectively through the skin as to be rapidly lost to the systemic circulatory systems, where the capsaicin solution is not entering the blood stream. Thus, the ideal vehicle would also enhance the skin's ability to retain the pharmacologically active ingredient.

As used herein, the term "pain-relieving amount" refers to the amount of any of the active ingredients of this invention that results in the reduction of pain following its administration to a subject.

As used herein, the term "subject" refers to all animals including humans. Examples of patients or subjects include humans, cows, dogs, cats, goats, sheep, and pigs. As used herein, the term "subject" may also be referred to as a "patient".

The terms "treating" or "treatment" includes, but is not limited to, the application of the patch comprising a composition comprising at least on active ingredient to the skin of a patient to prevent, reduce or inhibit the sensation of pain in the vicinity or region of the application of the patch. Further, the terms "treating" or "treatment" as used herein refer to reducing in severity and/or frequency of symptoms and/or their underlying cause of neuropathic pain.

II. Patches for Pain Reduction

The present invention provides patches comprising a low-dose capsaicin pharmaceutical composition, wherein the capsaicin may act as an analgesic. In this way, the capsaicin can provide a regional blockage of nervous pathways that carry pain signals, thereby reducing pain suffered by a subject.

As used herein, "pharmaceutical composition" means a "therapeutically effective amount" of the active ingredient, e.g., capsaicin, together with a pharmaceutically acceptable carrier or diluent. The pharmaceutical compositions of the present invention may be a sustained or extended-release composition or an immediate release composition comprising capsaicin. An example of a pharmaceutical composition of this invention includes a therapeutically effective amount of capsaicin in a physiologically acceptable vehicle. As used herein the term "pharmaceutical composition" may also be referred to herein as a "composition". The methods to prepare the compositions useful in the present invention are within the ordinary skill of persons in the art.

In one embodiment, a composition of this invention is administered to reduce the intensity of pain in a subject.

In one embodiment, this invention provides a patch for transdermal delivery of capsaicin for reducing pain comprising, a patch comprising a composition comprising a therapeutically effective amount of capsaicin, wherein the amount of capsaicin is less than about 8 percent by weight. In yet another embodiment, the amount of capsaicin is less than about 1 percent by weight. As used herein, the term "capsaicin" may also be referred to herein as the "analgesic".

The patches of this invention employ capsaicin as an active ingredient in a form capable of transdermal transport into the dermis or deeper. In one embodiment, the capsaicin can be formulated at least in part, as the free base. In another embodiment, capsaicin active ingredients can be formulated as neutralized pharmaceutically acceptable salt forms. Pharmaceutically acceptable salts include the acid addition salts, which are formed with inorganic acids such as, for example, hydrochloric, sulfuric or phosphoric acids, or such organic acids as acetic, oxalic, tartaric, mandelic, citric and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, etc.

The patch delivery system of this invention comprises a composition comprising a low-dose of capsaicin. As used herein, the terms "dose" or "dosage" refer to the measured quantity of an active ingredient administered at one time. As used herein, the term "dosage" may also herein be referred to as "dose" or "amount". In one embodiment, the composition comprises less than 4 percent capsaicin by weight. In one embodiment, the amount of capsaicin is between about 0.5 percent and about 2 percent. In another embodiment, the amount of capsaicin is about 8 percent. In yet another embodiment, the amount of capsaicin is about 2 percent.

As used herein, "high-dose" refers to concentrations of 6 to about 12 wt % capsaicin, sufficient to induce TRPV1-mediated terminal defunctionalization. "Low-dose" refers to concentrations below 4 wt %, which produce only partial TRPV1 desensitization and do not achieve terminal defunctionalization.

In yet another embodiment, the patches of the present invention can further include one or more additional compatible active ingredients which are aimed at providing the composition with another pharmaceutical effect in addition to that provided by capsaicin. "Compatible" as used herein means that the components of such a composition are capable of being combined with each other in a manner such that there is no interaction that would substantially reduce the efficacy of the composition under ordinary use conditions.

Such additional active ingredients include, but are not limited to penetration enhancers, and agents that reduce skin discomfort such as anti-inflammatory agents. In one embodiment, a combination of local anesthetics, such as are known in the art, can be comprised in a single patch.

In one embodiment, the patch of the present invention is infused with penetration enhancers or permeation enhancing agent which aid in treatment effectiveness by facilitating delivery of the capsaicin. The term "penetration enhancer" as used herein refers to an agent known to accelerate the delivery of a substance through the skin. Suitable penetration enhancers usable in the present invention include, but are not limited to, dimethylsulfoxide (DMSO), dimethyl formamide (DMF), allantoin, urazole, N,N-dimethylacetamide (DMA), decylmethylsulfoxide ($C_{10}$ MSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone™ from Whitby Research Incorporated, Richmond, Va.), alcohols including menthol, and the like. In one embodiment, the permeation enhancement agent is menthol.

The permeation enhancer may also be a vegetable oil. Such oils include, for example, safflower oil, cottonseed oil and corn oil. Additional penetration enhancers may generally be found in Remington's Pharmaceutical Sciences, 18th or 19th editions, published by the Mack Publishing Company of Easton, Pa. and Remington Essentials of Pharmaceutics, Linda B Felton, Pharmaceutical Press 2012, ISBN 978 0 85711105 0, both of which are fully incorporated by reference.

In one embodiment, the patch of this invention further comprises a permeation enhancement agent in an amount effective to enhance treatment. In certain embodiments, the permeation enhancement agent is a component of the composition. In alternate embodiments, the permeation enhancement agent is an active ingredient. In some embodiments, the composition of this invention comprises a permeation enhancement agent. In another embodiment, the permeation enhancement agent is menthol.

As used herein, the term "enhance treatment" refers to an amount of a permeation agent needed to enhance the permeation of an active ingredient, to enhance the reduction of pain experienced by a subject or to reduce side effects including skin discomfort resulting from administration of a patch of this invention, or any combination thereof. The term "enhance treatment" may herein also be referred to as "increase effective treatment". Enhanced treatment may result in an increase of an active ingredient permeating the skin. Alternatively, enhancement may result in a more rapid rate of an active ingredient permeating the skin then would occur without such treatment.

In one embodiment, a treatment-enhancing amount of a permeation enhancing agent can be about 1 percent to about 5 percent. In another embodiment, a treatment-enhancing amount of a permeation enhancing agent can be about 1 percent to about 16 percent. In yet another embodiment, a treatment-enhancing amount of a permeation enhancing agent can be about 3-5 percent, wherein these percentages are expressed as weight per weight of the composition comprised in the patch. In another embodiment, the permeation enhancement agent is menthol.

As used herein, reference of a percent amount of an active ingredient "by weight", herein refers to the percent expressed as weight per weight of the composition comprised in the patch.

The patch of the present invention also can be infused with an anti-inflammatory agent to reduce skin discomfort. As used herein "inflammation" refers to a response to infection and injury in which cells involved in detoxification and repair are mobilized to the compromised site by inflammatory mediators. Thus, the body's response may include edema, vasodilation, fever and pain. The term "skin discomfort" is used herein to refer to burning, stinging, itching, tingling, loss of feeling or heightened sensitivity of the skin. "Steroidal anti-inflammatory agent", as used herein, refer to any one of numerous compounds containing a 17-carbon 4-ring system and includes the sterols, various hormones (as anabolic steroids), and glycosides. Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof. In one embodiment, a patch of this invention includes at least one anti-inflammatory agent. In another embodiment, a patch of this invention does not include an anti-inflammatory agent.

Preferably, the additional active ingredients are added in a treatment-enhancing amount. As used herein a "treatment-enhancing amount" refers to an amount that is effective to accomplish the desired effect. Typically, such an effective amount is an amount between about 0.1 up to about 10 percent as weight per weight of the composition. More typically a treatment-enhancing amount would be between about 1 to about 5 percent. In one embodiment, the patch and methods of this invention comprise capsaicin and additional active ingredients in a treatment-enhancing amount.

Preferably, a treatment-enhancing amount of anti-inflammatory agent used to reduce skin discomfort is about 1 percent to about 5 percent, preferably about 1 percent to about 3 percent, and most preferably about 1 percent, wherein these percentages are expressed as weight per weight of the composition.

In other embodiment, the patch of the present invention can be used in conjunction with rehabilitation modalities, such as ultrasound, magnetophoresis, iontophoresis or a battery powered electronic stimulant. As used herein, the term "magnetophoresis" refers to the motion of dispersed magnetic particles relative to a fluid under the influence of a magnetic field. Magnetophoresis may provide enhancing drug delivery across biological barriers, including intact skin. Introduction of a drug or additional active ingredient through intact skin by the application of a direct electric current in iontophoresis may provide enhanced drug delivery when used in combination with a patch of this invention. In other embodiments, other patches described herein may be used in combination with iontophoresis. In one embodiment, iontophoresis acts as a transdermal delivery system in which a substance bearing a charge is propelled through the skin by a low electrical current. This method can be used to drive a drug across the skin barrier, as is done with pilocarpine to stimulate sweating in the sweat chloride test for cystic fibrosis. It can also be used in the reverse direction to draw a molecule such as glucose through the skin.

Methods utilizing electromotive enhancement treatments such as iontophoresis or magnetophoresis can provide faster relief to a subject, can increased an amount of an active ingredient penetrating into the skin or deeper tissue, can lead to an active ingredient penetrating deeper than the skin layers (epidermis, dermis), can provide longer relief from pain, can provide extended relief from pain or can provide stronger relief from pain, or any combination thereof. For example, in one embodiment, dependent on the strength of the charge used a drug may enter into skin and additionally into systemic circulation.

In an additional embodiment, the patch of the present invention can be used in conjunction with rehabilitation therapies, such as heat, massage, manipulation, strength and stretching exercises, to maximize healing results with the elimination of muscle pain and spasm.

III. Patch Administration for Treating Pain

Patches of the present invention have been described above. The patches can be administered at or adjacent to a site of pain to provide relief. In one embodiment, the pain is neuropathic pain, wherein administration of a patch of this invention reduces the neuropathic pain felt by a subject. In another embodiment, the pain is osteoarthritis pain, wherein administration of a patch of this invention reduces the osteoarthitic pain felt by a subject. In yet another embodiment, the pain is back pain, wherein administration of a patch of this invention reduces the back pain felt by a subject. In still another embodiment, the pain is a result of bone degeneration, wherein administration of a patch of this invention reduces the bone degeneration pain felt by a subject. In a further embodiment, the pain is associated with fibromyalgia, wherein administration of a patch of this invention reduces the pain associated with fibromyalgia felt by a subject. In another embodiment, the pain is associated with muscle strain, wherein administration of a patch of this invention reduces the muscle strain pain felt by a subject. In yet another embodiment, the pain is associated with muscle sprain, wherein administration of a patch of this invention reduces the muscle sprain pain felt by a subject. In still another embodiment, the pain is that associated with carpal tunnel syndrome pain, wherein administration of a patch of this invention reduces the carpal tunnel syndrome pain felt by a subject. In a further embodiment, the pain is that associated with any combination of diseases or disorders able to be relieved by local and/or deep tissue pain relief, wherein administration of a patch of this invention reduces the pain felt by a subject.

In one embodiment, a method for reducing pain in a subject comprises applying on a skin surface of the subject, at or near the site of pain, a patch comprising a capsaicin composition, wherein the application provides for transdermal delivery of an amount of capsaicin sufficient to reduce neuropathic pain in the subject. The methods of this invention may reduce pain resulting from different diseases, disorders or condition including neuropathic pain, deafferentation pain, osteoarthritis pain, rheumatoid arthritis (RA), post traumatic arthritis, lupus, juvenile, psoriatic arthritis (PsA), ankylosing spondylitis, psoriasis, systemic chronic inflammation with fibrosis, back pain, bone pain, pain associated with carpal tunnel syndrome, pain associated with fibromyalgia, pain from muscle strain or pain associated with muscle sprain or any combination thereof.

Neuropathic pain is a frequent component of chronic back pain, with epidemiologic studies indicating that approximately 15% to 25% of affected individuals experience predominantly neuropathic pain driven by nerve-root irritation, radiculopathy, or segmental sensory pathway injury. In addition, 20% to 40% of back-pain sufferers exhibit a mixed pain phenotype in which neuropathic mechanisms coexist with nociceptive contributors such as disc degeneration, facet arthropathy, or ligamentous strain. Within these neuropathic and mixed cohorts, deafferentation plays a meaningful role: compression, traction, or injury of dorsal roots and associated sensory branches can produce partial loss of afferent input, leading to characteristic numbness, paresthesias, and persistent neuropathic pain despite structural stabilization. As a result, a substantial proportion of chronic back-pain patients present with pain states involving exclusive neuropathic features, mixed neuropathic-nociceptive mechanisms, or local deafferentation, emphasizing the need for therapeutic approaches that can modulate both peripheral nociceptive signaling and sensory-nerve dysfunction in dermatomes.

As used herein, the term "administration" refers to applying, e.g., adhering a patch comprising a capsaicin formulation on a skin surface of a subject.

In one embodiment, administration of a patch provides immediate or nearly immediate relief, e.g., reduction of pain. In another embodiment, administration of a patch provides long term relief, e.g., reduction of pain. In another embodiment, administration of a patch provides both immediate or nearly immediate and long-term pain relief.

The patches described herein can be administered at or adjacent to the sites of pain to provide relief. The patches can be administered once a day, for example, for fast, long term pain relief, e.g., pain relief starts relatively quickly and is maintained over an extended period of time. As used herein the terms "reduction of pain" and "pain relief" are interchangeable with all the same meanings. In one embodiment, application of a patch may reduce the pain suffered by a subject completely or almost completely. In another embodiment, application of a patch may reduce the pain suffered by a subject by about 50 to almost 100 percent. In yet another embodiment, application of a patch may reduce the pain suffered by a subject by about 50 to 90 percent. In still another embodiment, application of a patch may reduce the pain suffered by a subject by about 80 to 90 percent.

In a further embodiment, application of a patch may reduce the pain suffered by a subject by about 70 to 80 percent. In one embodiment, application of a patch may reduce the pain suffered by a subject by about 50 to 70 percent. In still another embodiment, application of a patch may reduce the pain suffered by a subject by less than 50 percent.

In one embodiment a patch of this invention is applied for between about 5 minutes to about 120 minutes. In one embodiment a patch is applied for about 8 hours. In another embodiment a patch is applied for about 9 hours. In yet another embodiment, a patch is applied for about 10 hours. In still another embodiment, a patch is applied for about 12 hours. In a further embodiment, a patch is applied for about 24 hours.

A patch of the present invention is applied on the skin surface at a site or adjacent to a painful region. In some embodiments, multiple patches may be applied at the same time. Patches may be applied in the same region, an adjacent region or regions distal from one another. Fresh patches may be reapplied after a 24-hour period.

In some embodiments, the patch is applied to the painful skin and subcutaneous structures in order to effect pain relief while avoiding the side effects associated with systemic delivery. Pain relief is obtained within minutes to hours and lasts for periods of approximately three to six hours to 24 hours. The patches are applied such that the dosage is sufficient to provide an effective dose in the painful area or immediately adjacent areas, to ameliorate or eliminate pain and other unpleasant sensations such as itching. In one embodiment, pain is reduced for at least 12 hours. In another embodiment, pain is reduced for at least 24 hours. In yet another embodiment, pain is reduced for more than 24 hours.

In yet another embodiment, pain is reduced for more than about 1 week. In yet another embodiment, pain is reduced for about more than 1 month. In yet another embodiment, pain is reduced for about more than 3 months. The appropriate dosages for pain treatment by way of patches of the present invention are determined by a variety of factors. The rate at which the active components are absorbed is a function of skin permeability. Skin permeability varies between different sites on a patient's body and depends on the thickness of the stratum corneum. The stratum corneum is the outer-most layer of skin and is the main source of penetration and permeation resistance for dermally administered drugs. For example, the permeability, in general, increases in order from planter foot arch, lateral ankle, palm, ventral forearm, dorsal forearm, back, chest, thigh, abdomen, scalp, axilla, forehead, and scrotum; see R. C. Wester. & H. I. Maibach, Regional variation in Percutaneous Absorption, in Percutaneous Absorption, Mechanism, Methodology, Drug Delivery 111-119 (R. L. Bronaugh & H. I. Maibach eds., 2nd ed. 1989), hereby expressly incorporated in full herein by reference.

The delivery rate of an active ingredient from a patch, e.g., capsaicin, of the present invention that is required for proper pain relief is determined by a variety of factors. One important factor regarding delivery rate is the surface areas of the active ingredients in contact with a patient's skin. In general, the larger the contact surface area, the higher the rate of delivery. Different delivery rates of an active ingredient may be needed depending on the severity of pain felt. The surface areas of components can adjust to provide the desired delivery rate of an active ingredient to a patient.

In addition, delivery rate may be enhanced as describe above using chemical enhancement agents, for example menthol and/or physical enhancement methodologies, for example iontophoresis, a battery powered electronic stimulant or magnetophoresis. In one embodiment, methods of this invention for reducing neuropathic pain include treatment enhancing amounts of a permeation agent. In one embodiment, methods of this invention for reducing neuropathic pain include treatment enhancing methodologies including iontophoresis, a battery powered electronic stimulant or magnetophoresis.

Methods of this invention include transdermal administration of active ingredients, e.g., capsaicin. In one embodiment, methods of this invention for reducing pain in a subject comprise applying on a skin surface of the subject, at or near the site of pain a patch comprising compositions comprising capsaicin at less than about 8 percent by weight.

In another embodiment, methods of this invention use capsaicin at between about 0.2 percent and about 1 percent by weight. In yet another embodiment, methods of this invention use capsaicin at about 1 percent by weight. In still another embodiment, methods of this invention use capsaicin at about 2 percent by weight. In a further embodiment, methods of this invention use capsaicin at about 3 percent by weight. In one embodiment, methods of this invention use capsaicin at about 3.95 percent by weight.

In one embodiment the composition of this invention comprises local anesthetic and drugs not traditionally associated with TRPV1 receptor agonist properties but which have a local anesthetic effect. Non limiting examples of such drugs include for example, non-narcotic analgesics, such as, acetylsalicylic acid, ketoprofen, piroxicam, diclofenac, indomethacin, ketorolac, rofecoxib, and celecoxib, and pharmaceutically acceptable salts thereof, or mixtures thereof.

As used herein the term "drug" refers to a substance used in the diagnosis, treatment, or prevention of a disease or medical condition or an active component of a medication. Of course, the term "drug" encompasses capsaicin, local anesthetics and/or analgesics.

A patch may be applied to the skin surface for an effective time period. For effective use, a patch should be in contact with a surface of the skin and remain in place for the duration of the treatment. In order that a patch remains in place, an adhesive may be comprised as part of a patch. Alternatively, an adhesive, such as an adhesive strip or tape may be used to hold the patch in place. For example, a patch may be adhered to a patient's back through the use of a drug-in-adhesive patch. In an alternative example, a patch may both included an adhesive and be perforated to allow the patch to stretch, wherein a patch may be wrapped around a subject's body appendage, e.g., a leg, arm, finger, head or neck.

The selected patch may comprise a composition comprising permeation enhancers. Alternatively, physical methodologies such as iontophoresis, a battery powered electronic stimulant or magnetophoresis may be used to enhance the permeation of at least one active ingredient. Technique using a electric charge to deliver active ingredient through the skin, may enhance permeation of at least one active ingredient. The process is a noninvasive method of propelling high concentrations of a charged substance, e.g., capsaicin, transdermally by repulsive electromotive force using a electrical charge applied to an iontophoretic chamber containing a similarly charged active agent and its vehicle.

Following the recommended time period of application, the patch may be removed from the skin surface. Relief from pain may continue even though the patch has been removed. Following a period of 24 from the initial administration, this cycle of use may be employed by a subject. This may be significant for sufferers of chronic pain.

In one embodiment, the term "a" or "one" or "an" refers to at least one. As used in the specification and claims, the forms "a," "an" and "the" include singular as well as plural references unless the context clearly dictates otherwise.

In one embodiment the phrase "two or more" may be of any denomination, which will suit a particular purpose. In one embodiment, "about" may comprise a deviance from the indicated term of +1%, or in some embodiments, −1%, or in some embodiments, +2.5%, or in some embodiments, +5%, or in some embodiments, +7.5%, or in some embodiments, +10%, or in some embodiments, +15%, or in some embodiments, +20%, or in some embodiments, +25%, or in some embodiments, +50%.

While certain features of the invention have been illustrated and described herein, many modifications, substitutions, changes, and equivalents will now occur to those of ordinary skill in the art. It is, therefore, to be understood that the appended claims are intended to cover all such modifications as fall within the spirit of the invention.

The invention claimed is:

1. A method of treating post-herpetic neuralgia (PHN) pain in a subject, comprising: applying a patch to a skin surface, the patch comprising about 8 wt % capsaicin, wherein the PHN comprises partial or complete deafferentation of a sensory pathway.

2. A method of treating post-surgical neuropathic pain in a subject, comprising: applying a patch to a skin surface, the patch comprising about 8 wt % capsaicin, wherein the post-surgical neuropathic pain comprises central neuropathic pain.

3. The method of claim 2, wherein the central neuropathic pain comprises a partial or complete deafferentation of a sensory pathway.

4. The method of claim 3, wherein the surgical procedure consists of hip surgery.

5. The method of claim 3, wherein the surgical procedure comprises surgery for post-traumatic arthritis.

6. A method for treating chronic back pain in a subject without a spinal cord injury, comprising: applying a patch to a skin surface, the patch comprising capsaicin.

7. The method of claim 6, wherein the chronic back pain comprises pain from microarchitectural bone changes, and wherein the patch comprises a therapeutically effective dose of less than 0.5 wt % capsaicin.

8. The method of claim 6, wherein the chronic back pain comprises a central neuropathic pain and wherein the patch comprises about 8 wt % capsaicin.

9. The method of claim 8, wherein the central neuropathic pain comprises a partial of full deafferentation of a sensory pathway.

* * * * *